United States Patent [19]

Hink, Jr.

[11] Patent Number: 4,554,251

[45] Date of Patent: Nov. 19, 1985

[54] PROCESS AND MEDIUM FOR CULTURING ANT VENOM GLAND CELLS

[75] Inventor: Walter F. Hink, Jr., Columbus, Ohio

[73] Assignee: The Ohio State University Research Foundation, Columbus, Ohio

[21] Appl. No.: 549,170

[22] Filed: Nov. 7, 1983

[51] Int. Cl.$^4$ .......................... C12N 5/00; C12P 1/00; C12R 1/91; A01N 63/02; A61K 35/58

[52] U.S. Cl. ..................................... 435/240; 435/41; 435/948; 424/95; 424/98

[58] Field of Search ...................... 435/1, 41, 240, 241; 424/95, 98

[56] References Cited

PUBLICATIONS

Miltenberger, H. G. (1983), Chem Abst. 100:118039f.
Marks, E. P. (1979), Chem Abst. 90:183456d.
Wilkinson, C. F. (1979), Chem Abst. 90:183457e.
Mitsuhashi, J. (1979), Chem Abst. 93:235655b.
Arthritis and Rheumatism, 25(4), Supplement Abstract C88, (Apr. 1982).

Proceedings of the North Sea Central Branch, Entomological Society of America 27, 153 (1972).
Chapter 28, Kursbak and Maramorosch (eds.), Invertebrate Tissue Culture, Academic Press (1976).

Primary Examiner—Thomas G. Wiseman
Assistant Examiner—R. Thomas Gallegos
Attorney, Agent, or Firm—Sidney W. Millard

[57] ABSTRACT

In vitro culture of the venom gland cells of the ant *Pseudomyremex triplarinus* is effected by removing venom gland tissue from a larva or pupa of *P. triplarinus* subjecting the tissue to a protease to separate out the cells therein and culturing the resultant cells in an isotonic saline medium comprising carbohydrate, amino acids guanosine 3',5'-cyclic monophosphate and adenosine 3',5'-cyclic monophosphoric acid, at least part of the medium having been conditioned with *Spodoptera frugiperda* cells. Such in vitro culture provides a practicable route to volume production of the biologically active materials which are useful for treating the symptoms of rheumatoid arthritis and which the venom gland cells are known to produce.

39 Claims, No Drawings

PROCESS AND MEDIUM FOR CULTURING ANT VENOM GLAND CELLS

BACKGROUND OF THE INVENTION

This invention relates to a process and medium for culturing ant venom gland cells. More particularly, this invention relates to a process, cell culture and cell culture medium for in vitro culture of cells of the venom gland of the ant *Pseudomyrmex triplarinus*.

The cells of the venom gland of the ant, *Pseudomyrmex triplarinus* are known to produce biologically active materials which are useful in treating the symptoms of rheumatoid arthritis; see, for example, U.S. Pat. No. 4,247,540 issued Jan. 27, 1981 to Holzmann, and Arthritis and Rheumatism, 25(4), Supplement, Abstract C88 (Apr. 1982). However, the extraction of the venom gland cells from *P. triplarinus* is such a tedious, time-consuming and expensive operation the extraction of sufficient cells even for experimental purposes is a formidable proposition, while production of the biologically active material on a commercial scale is out of the question without some process for culturing the venom gland cells in vitro. Hitherto, no such process for in vitro culture of the venom gland cells has been available. This invention provides a process for culturing such cells in vitro, the resultant cell culture, and a cell culture medium for use in the process.

SUMMARY OF THE INVENTION

The invention provides a process for culturing cells of the venom gland of the ant, *Pseudomyrmex triplarinus*, this process comprising removing venom gland tissue from a member of the species *Pseudomyrmex triplarinus*, subjecting the tissue thus removed to the action of a protease and separating the individual cells in the tissue from one another. The cells are then cultured in a cell culture medium substantially isotonic with the cells, this medium comprising carbohydrate, amino acids, adenosine 3',5'-cyclic monophosphoric acid, isoproterenol, guanosine 3',5'-cyclic monophosphate, hydrocortisone, epidermal growth factor, fibroblast growth factor, insulin, transferrin and a source of assimilable selenium. Prior to contact with the venom gland cells, at least part of the culture medium is conditioned with *Spodoptera frugiperda* cells.

The invention also provides a cell culture comprising a plurality of cells from the venom gland of *Pseudomyrmex triplarinus* in contact with the aforementioned cell culture medium.

Finally, the invention provides a cell culture medium having an osmotic pressure of substantially 500 milliosmols, this medium comprising carbohydrate, amino acids, adenosine 3',5'-cyclic monophosphonic acid, isoproterenol, guanosine 3',5'-cyclic monophosphate, hydrocortisone, epidermal growth factor, fibroblast growth factor, insulin, transferin and a source of assimilable selenium.

DETAILED DESCRIPTION OF THE INVENTION

As already mentioned, the in vitro cell culture process of the invention involves removing venom gland tissue from the ant, subjecting this tissue to a protease, separating the cells of the tissue from one another and then culturing the cells in a cell culture medium. Preferably the venom gland tissue is removed from a larva or pupa of *P. triplarinus*; although the venom gland cells present in the adult ants can readily be dissected out, the use of adult ants is not recommended since their venom gland cells deteriorate rapidly in a culture. The preferred protease for use in the process is trypsin. I have tested hylauronidase, collagenase and pronase, but have found that trypsin does the least damage to the venom gland cells. It is preferred that the cells be subjected to the action of trypsin in a saline medium substantially free of calcium and magnesium ions. The presently preferred technique for the protease treatment comprises exposing the venom gland tissue to the trypsin in the calcium-and magnesium-free saline medium for at least about 12 hours at a temperature not in excess of about 10° C., then adding a trypsin inhibitor to inhibit the trypsin and teasing the tissue apart to disassociate the cells therein. (Although the temperature at which the venom glands are treated with the trypsin is well below the optimum temperature for the enzymatic activity of trypsin, the use of this relatively low temperature is desirable since less damage is caused to the cell membranes at such low temperatures.)

Typically from 3 to 8 venom glands provide an adequate number of cells to produce a proper cell culture.

As already mentioned, the essential components of the cell culture medium are carbohydrates, amino acids, adenosine 3',5'-cyclic monophosphoric acid, isoproterenol, guanosine 3',5'-cyclic monophosphate, hydrocortisone, epidermal growth factor, fibroblast growth factor, insulin, transferin and assimilable selenium; it has been found empirically that all these materials are needed for long-term viability of the vernom gland cells in culture.

The carbohydrate used in the culture medium is preferably a sugar and desirably comprises at least one of the sugars fructose, glucose and sucrose. It is preferred that the culture medium contain a total of at least about 5 g/l. of these sugars. It is also preferred that the amino acids in the culture medium comprise the levo isomers of alanine, arginine, asparagine, aspartic acid, glutamic acid, glutamine, glycine, histidine, isoleucine, leucine, lysine, methionine, phenylalanine, proline, serine, threonine, tryptophan, valine, tyrosine and cystine and that the medium comprise at least about 4 g/l of amino acids. The concentration of guanosine 3',5'-cyclic monophosphate is desirably at least about 0.1 mg/l and that of adenosine 3',5'-cyclic monophosphoric acid, preferably of at least about 4 g/l. It is preferred that the cell culture medium comprise at least 0.01 mg/l. of isoproterenol, at least 10 mg/l. of insulin, and at least $10^{-7}$ g/l. of hydrocortisone.

The epidermal growth factor included in the instant culture medium is a naturally occuring growth factor. The material is available commercially from Collaborative Research, Inc., 1365 Main Street, Waltham, Mass. 02154 and is isolated from male mouse submaxillary glands. The growth factor is known to be mitogenic for a wide variety of epidermal cells, both in organ and cell culture, and for some non-epidermal cells. The growth factor has been completely characterized, possessing a molecular weight of 6,100 and an isoelectric point of 4.6; the commercial product shows only a single band on SDS disc-gel electrophoresis. The instant culture medium desirably contains at least $10^{-7}$ g/l. of the epidermal growth factor.

The fibroblast growth factor used in the instant cell culture medium is also a naturally occuring growth factor and is available commercially from Collaborative Research, Inc. The commercial material is isolated from bovine pituitary glands and purified by acid and ammonium sulfate precipitation followed by dialysis, ion exchange chromatography and gel exclusion chromatography. The growth factor has been completely characterized, having a molecular weight of 13,400 and an isoelectric point of 9.5; the commercial material shows only a single band on SDS discgel eletrophoresis. The instant cell culture medium desirably comprises at least 0.01 mg/l. of fibroblast growth factor.

The transferrin used in the instant culture medium is conveniently iron-saturated human transferrin, which is available commercially from Collaborative Research, Inc. The cell culture medium desirably contains at least 1 mg/l. of transferrin.

As already mentioned, the instant cell culture medium must also contain a source of assimilable selenium. A convenient source of assimilable selenium is an alkali metal selenate, conveniently sodium selenate prepared by neutralizing selenous acid with sodium hydroxide. The cell culture medium desirably contains at least 1 mg/l. of selenium.

The pH of the instant cell culture medium must be about 7. Those skilled in the art will appreciate that, as in most biological systems, some minor variations in pH are permissible without killing or otherwise adversely affecting the cells being cultured, but that the pH range for cell culture is fairly narrow and any great deviation in pH 7 will kill or at least adversely effect the cells. It will also be apparent to those skilled in the art that the extent of permissible pH variation can easily be determined by routine empirical test. To maintain the cells at the optimum pH it is of course in practice necessary to employ a buffer in the cell culture medium, and a preferred buffer for this purpose is N,N-bis[2-hydroxyethyl]aminoethane sulfonic acid. It has been found desirable to use relatively high concentrations of this buffer, at least 0.1M.

The cell culture medium must be substantially isotonic with the cell; by the phrase "substantially isotonic" is meant only that the osmotic pressure of the cell culture medium must be sufficiently close to the osmotic pressure within the cells, that the cells neither gain or lose quantities of fluid sufficient to prevent growth of these cells. The osmotic pressure of ant hemolymph as measured by a microosmometer varies from about 400 to about 550 milliosmols, and in practice it has been found that using a cell culture medium with a relatively high osmotic pressure of about 500 milliosmols gives optimum results.

The cell culture medium also desirably contains sodium, potassium, magnesium, calcium, chloride, sulfate and othophosphate ions, at least one of the polycarboxylic acids citric, alpha-ketoglutaric, fumaric, malic and succinic acids and one or more of the vitamins thiamine, riboflavin, pantothenic acid, pyridoxine, p-aminobenzoic acid, folic acid, niacin, isoinositol and biotin. Other preferred components of these cell culture mediums include choline and at least one protein, preferably one or more of the proteins bovine plasma albumin, fetal bovine serum, TC yeastolate (TC yeastolate is available commercially from Difco and is the soluble portion of autolyzed fresh yeast) and lactalbumin hydrolysate. The culture medium also desirably contains at least about 0.01 mg/l of pyridoxal, at least about 1 g/l of trehalose and an anti-bacterial agent, preferably garamycin.

An especially preferred culture medium for use in the instant process has substantially the following composition:

| | mg/l. |
|---|---|
| $Na^+$ | 436 |
| $K^+$ | 1192 |
| $Mg^{2+}$ | 270 |
| $Ca^{2+}$ | 300 |
| $SO_4^{2-}$ | 1067 |
| $PO_4^{3-}$ | 312 |
| Fructose | 1700 |
| Glucose | 4400 |
| Sucrose | 400 |
| L-alanine | 145 |
| L-arginine | 133 |
| L-asparagine (as monohydrate) | 380 |
| L-aspartic acid | 320 |
| L-glutamic acid | 929 |
| L-glutamine | 1620 |
| L-glycine | 872 |
| L-histidine | 371 |
| L-isoleucine | 191 |
| L-leucine | 197 |
| L-lysine (as hydrochloride) | 1638 |
| L-methionine | 74 |
| L-phenylalanine | 120 |
| L-proline | 350 |
| L-serine | 136 |
| L-threonine | 613 |
| L-tryptophan | 100 |
| L-valine | 475 |
| L-tyrosine | 30 |
| L-cystine | 80 |
| Citric acid | 500 |
| Alpha-ketoglutaric acid | 450 |
| Fumaric acid | 550 |
| Malic acid | 670 |
| Succinic acid | 660 |
| Thiamine (as hydrochloride) | 0.02 |
| Riboflavin | 0.02 |
| Pantothenic acid (as Ca salt) | 0.02 |
| Pyridoxine (as hydrochloride) | 0.02 |
| p-Aminobenzoic acid | 0.02 |
| Folic acid | 0.02 |
| Niacin | 0.02 |
| Isoinositol | 0.02 |
| Biotin | 0.01 |
| Choline chloride | 20 |
| BES(N,N—bis[2-hydroxymethyl]-2-aminoethane sulfonic acid) | 17000 |
| Bovine plasma albumin | 10 |
| Fetal bovine serum | 50 ml |
| TC yeastolate | 3000 |
| Lactalbumin hydrolysate | 3000 |
| Epidermal growth factor | 0.0018 |
| Insulin | 105 |
| Transferrin | 5 |
| Selenium | 5 |
| Trehalose | 2000 |
| Fibroblast growth factor | 0.025 |
| Hydrocortisone | 0.0002 |
| Guanosine 3',5'-cyclic monophosphate (cGMP) | 0.35 |
| Garamycin | 50 |
| Adenosine 3',5-cyclic monophosphoric acid (cAMP) | 8780 |
| Isoproterenol | 0.0125 |
| Pyridoxal | 0.02 |

In as much as the exact nutritional requirements for culturing venom gland cells of *Pseudomyrmex triplarinus* are not at present precisely known, it may eventually be found that certain of the suggested components of the culture medium described above are not in fact necessary; for example, it is quite likely that the cells can in fact survive without one or more of the amino acids already mentioned. However, it does appear that the presence of adenosine 3',5'-cyclic monophosphoric acid is essential for long-term viability of the cell culture and it also appears that conditioning of at least part of the culture medium with *Spodoptera frugiperda* cells prior to contact of the medium with the venom gland cells is also essential for long-term cell culture. As those skilled in the art are aware, in vitro culturing of various types of cells is often carried out more efficiently after conditioning of at least part of the medium employed with other cells. It is generally believed (although the invention is in no way limited by this belief) that the pre-conditioning with *S. frugiperda* cells releases into the culture medium certain factors, whose precise nature is as yet unknown, which serve to assist the growth of the cells which are later cultured in the medium.

Culturing of the cells using the aforementioned medium may be conducted at 25°–30° C.; the optimum temperature appears to be about 28° C. Desirably, spent medium is removed from the cells and fresh medium added about every 4–5 days.

The following Example is now given, though by way of illustration only, to show details of the presently-preferred process, cell culture and cell culture medium of the invention.

EXAMPLE

(A) Preparation of Larvae and Pupae

Fine tweezers were sterilized by soaking in 1.0% sodium hypochlorite solution, rinsing in two containers of sterile water and finally rinsing in 95% ethanol. Larvae and pupae of *Pseudomyrmex triplarinus* were surface sterilized by immersion in an aqueous solution containing 1.0% of sodium hypochlorite and 0.0005% of Triton X-100 (a surface-active agent) for 90 seconds. The larvae and pupae were then removed from the sterilizing solution, rinsed four times in sterile water and transferred to sterile blotting paper in Petri dishes for drying.

(B) Removal of Venom Gland Tissue from Larvae

A drop of unconditioned culture medium (the composition of which is described below) was placed in a Petri dish and a larva placed in the dish. Dissection of the larva was effected with two pairs of fine tweezers sterilized as described in part (A) of the Example. The larva was held tightly midway down its body with one pair of the tweezers and the cuticle torn away from the last few segments of the larva's body with other pair of tweezers. The fat bodies were then moved aside so that the imaginal tissue could be seen. In the older larvae, the venom gland tissue is attached to the vulvulae, while in younger larvae no vulvulae are present and the venom gland tissue is attached to the cuticle. In either case, the venom gland tissue was removed with one pair of the tweezers and then subjected to treatment with trypsin as described in (D) of this Example.

(C) Removal of Venom Gland Tissue from Pupae

Again, dissection of pupae was effected using two pairs of fine tweezers sterilized as described in part (A) of this Example. A drop of cell culture medium was placed in a Petri dish and a pupa was placed next to it. The abdomen of the pupa was grasped near the constriction with one pair of tweezers while the other pair were used to grasp the tissue at the base of the stinger. Both pairs of tweezers were then pulled slowly until the venom reservoir was visible. The reservoir was then pulled so that the duct between it and the stinger were severed, care being taken that the hindgut was not ruptured. The venon reservoir was then pulled further straight back parallel to the axis of the pupa until the free venom glands were teased away from the reservoir. The venom gland tissue thus dissected out was then treated with trypsin as described in part (D) of this Example.

(D) Separation of Cells in Venom Gland Tissue

The following calcium-and magnesium-free solution was used in this part of the process:

|  | g/l. |
|---|---|
| sodium bicarbonate | 0.588 |
| potassium chloride | 2.02878 |
| sodium chloride | 0.140 |
| potassium dihydrogen phosphate | 0.44774 |
| glucose | 40.2 |

Before use, the pH of this solution was adjusted to 6.8 with 1N hydrochloric acid.

The venom gland was placed in a standing drop of this medium to which 0.25% by weight of trypsin had been added and left for 22 hours at 4° C. The trypsin-containing medium was then removed and 0.1 ml. of the medium to which 0.1% by weight of soybean trypsin inhibitor had been added was placed on the venom gland tissue to stop the action of any remaining trypsin. The venom gland tissue was then transferred, using tweezers, to a standing drop of the cell culture medium and teased apart to separate the cells therein.

(E) Preparation of Unconditioned Cell Culture Medium

An unconditioned cell culture medium was prepared having the following composition:

|  | mg/l. |
|---|---|
| salts | |
| sodium bicarbonate | 588.0 |
| potassium chloride | 2028.78 |
| magnesium sulfate heptahydrate | 2738.0 |
| potassuim dihydrogen phosphate | 447.74 |
| sodium chloride | 699.76 |
| calcium chloride dihydrate | 1101.0 |
| sugars | |
| fructose | 7200.0 |
| glucose | 4400.0 |
| sucrose | 400.0 |
| amino acids | |
| L-alanine | 145.39 |
| L-arginine | 132.57 |
| L-asparagine.H$_2$O | 380.0 |
| L-aspartic acid | 320.0 |
| L-glutamic acid | 929.32 |
| L-glutamine | 1620.00 |
| L-glycine | 871.79 |
| L-histidine | 371.45 |
| L-isoleucine | 190.74 |
| L-leucine | 197.03 |
| L-lysine hydrochloride | 1637.91 |
| L-methionine | 74.01 |
| L-phenylalanine | 120.0 |
| L-proline | 350.0 |
| L-serine | 135.88 |
| L-threonine | 613.23 |
| L-tryptophan | 100.0 |
| L-valine | 474.57 |
| L-tyrosine | 30.0 |
| L-cystine | 80.0 |
| polycarboxylic acids | |
| citric acid | 500.0 |
| alpha-ketoglutaric acid | 450.0 |
| fumaric acid | 550.0 |
| malic acid | 670.0 |
| succinic acid | 660.0 |
| vitamins | |
| thiamine hydrochloride | 0.02 |
| riboflavin | 0.02 |

-continued

|  | mg/l. |
| --- | --- |
| calcium pantothenate | 0.02 |
| pyridoxine hydrochloride | 0.02 |
| p-amino benzoic acid | 0.02 |
| folic acid | 0.02 |
| niacin | 0.02 |
| isoinositol | 0.02 |
| biotin | 0.01 |
| choline chloride | 20.02 |
| BES | 4.266 |
| proteins |  |
| bovine plasma albumin | 10.0 |
| fetal bovine serum | 50.0 ml. |
| TC yeastolate | 3000.0 |
| lactalbumin hydrolysate | 3000.0 |

This unconditioned cell culture medium is a modification of a medium originally designed for culture of honey bee tissue cells (see Hink, In vitro culture of cells and tissues from the honey bee, *Apis mellifera*, Proc. North Central Branch, Entomological Society of America, 27:153 (1972)).

To produce one liter of this unconditioned culture medium, the amino acids other than the tyrosine and cystine were dissolved in 700 ml of tissue culture water in a 4 liter beaker and stirred with a magnetic stirrer. Once all these amino acids had been dissolved, the sugars were dissolved in the amino acid solution. Next, the salts (other than the calcium chloride) were dissolved in the mixed amino acid/sugar solution by weighing out each salt separately and dissolving it in the amino acid/sugar solution. The salts were added to the amino acid/sugar solution separately in the order given in the above table, each salt being completely dissolved in the amino acid/sugar solution before the next salt was added to prevent formation of undesirable precipitates. The calcium chloride dihydrate was then dissolved separately in 10 ml. of tissue culture water and this calcium chloride solution added to the mixed solution. The tyrosine was then dissolved in 2.0 ml. of 1N hydrochloric acid, the cystine dissolved in this acidified tyrosine solution and the resultant tyrosine/cystine solution added to the mixed solution prepared as described above.

The polycarboxylic acids were dissolved in 150 ml. of tissue water, the pH of this solution adjusted to 6.6 with 1N sodium hydroxide solution and the resultant alkaline solution added to the aforementioned mixed solution. Next, the choline chloride was dissolved in 10 ml. of tissue culture water and the resultant solution added to the mixed solution, followed by the BES. The vitamins were made up in a solution having 1,000× the final concentration, and 1.0 ml. of this concentrated vitamin solution was added to the mixed solution following the addition of the BES. The pH of the solution was then adjusted to 6.6 with 1N sodium hydroxide solution, the volume adjusted to 1 liter with tissue culture water and the resultant solution sterilized by filtering through a 0.22 micron filter. The lactalbumin hydrolyzate, TC yeastolate, bovine plasma albumin and fetal bovine serum (heat inactivated) were added to the solution and the solution stirred until all the ingredients were dissolved. The pH was adjusted to 6.25 with 1N hydrochloric acid and the solution resterilized by filtering through a 0.22 micrometer filter. The resultant medium may be stored at 5° C. for many months and should have an osmotic pressure of about 330 milliosmols, which is acceptable for *S. frugiperda* cells. The medium is now ready for conditioning.

(F) Conditioning of Culture Medium

For conditioning the instant culture medium, there are used *Spodoptera frugiperda* cells grown in a conventional TNM-FH medium; the cells used were from cultures 3–4 days old which had been grown to a density of $2-3 \times 10^6$ cells/ml. (TNM-FH medium is a complex cell culture medium described in Hink and Strauss, "Growth of the *Trichoplusia ni* (TN-368) cell line in suspension culture", which comprises Chapter 28 of Kurstak and Maramorosch (eds.), Invertebrate tissue culture, Academic Press, 1976). The *S. frugiperda* cells were subcultured into the unconditioned instant culture medium so that the initial cell density was 200,000 cells/ml.; 15.0 ml. aliquots of the instant culture medium were conditioned in separate 75 cm.$^2$ tissue culture flasks. The flasks were incubated for 72 hours and the medium then removed from the flasks and placed in centrifuge tubes. The tubes were centrifuged at 500 xg. for 10 minutes to precipitate all cells, the supernatant medium removed from the cells (the supernatant from various tubes being combined for obvious reasons) and the pH of the medium adjusted to 7.0 with 1N potassium hydroxide solution. Finally, the medium was sterilized by filtration through a 0.22 micrometer filter to produce the conditioned instant medium.

(G) Preparation of Final Culture Media

Unconditioned culture medium prepared as described in (E) of this example was combined in a ratio of 1:1 v/v with conditioned culture medium prepared as described in part (F) of the Example, and the pH of the rsultant mixture adjusted to 7. The following additives were then added to this mixture of conditioned and unconditioned culture medium to prepare the final culture medium:

|  | mg/l. |
| --- | --- |
| epidermal growth factor | 0.0018 |
| insulin | 105.0 |
| transferrin | 5.0 |
| selenium | 5.0 |
| trehalose | 2000.0 |
| fibroblast growth factor | 0.025 |
| hydrocortisone | 0.0002 |
| guanosine 3',5'-cyclic monophosphate | 0.3673 |
| garamycin | 50.0 |
| BES | 17064 |
| isoproterenol | 0.0125 |
| cAMP | 8780 |
| pyridoxal | 0.02 |

(H) Culturing of Cells

Separated cells as prepared as described in part (D) of this Example were placed in each of the final culture media described above and cultured at 28° C. in sealed, humidified containers in an incubator to prevent evaporation. The cultures were refed with fresh medium after 24 hours and thereafter routinely refed every 4–5 days, refeeding being accomplished by pipeting the spent medium from the cells with fine Pasteur pipets and adding of fresh medium. The venom gland cells multiplied readily under these conditions and could be kept alive for at least one year. The cells could also be transferred to other culture dishes where they continued to multiply.

To confirm that cells cultured in the manner described above do produce the desired biologically active material, samples of cell medium taken after cells had begun to grow therein were submitted to the Carrageenan Paw Edema Assay, which is known to be a useful animal model to test the effects of anti-inflammatory agents intended for use in humans.

Groups of six male Sprague-Dawley rats were injected subcutaneously with either the tissue culture medium or with ant venom glands suspended in 1% methocel. Two hours later, the right paw was injected subcutaneously with 0.1 ml. of 1% carrageenan. The paw volume was measured immediately after the carrageenan injection and three hours later, and the percentage inhibition of edema calculated. (Obviously, it is necessary to provide a control group to determine the degree of edema in the absence of an anti-inflammatory agent.) The results obtained are shown in the table below.

TABLE

| Product | Dose (ml) | % Inhib. |
|---|---|---|
| Venom Glands | 0.25 | 54.3 |
|  | 0.5 | 92.6 |
| Tissue Culture Media* |  |  |
| From Pupae Cells | 1.0 | 25.4 |
| From Larva Cells | 1.0 | 25.4 |

*Samples were taken of media after cells had started to grow.

The foregoing data indicate that the cell cultures do contain biologically active material useful for treating the symptoms of rheumatoid arthritis.

It will be apparent to those skilled in the art that numerous changes and modifications may be made in the preferred embodiments of the invention described above without departing from the scope of the invention. Accordingly, the foregoing description is to be construed in an illustrative and not in a limitative sense, the scope of the invention being defined solely by the appended claims.

I claim:

1. A process for culturing cells of the venom gland of the ant, Pseudomyrmex triplarinus, which process comprises:
   removing venom gland tissue from a member of the species Pseudomyrmex triplarinus;
   subjecting said removed venom gland tissue to the action of a protease and separating the individual cells in said venom gland tissue from one another;
   culturing said separated cells in a cell culture medium substantially isotonic with said cells, said medium having a pH of about 7 and comprising at least about 5 g/l of carbohydrate, at least about 4 g/l of amino acids, at least about 4 g/l of adenosine 3',5'-cyclic monophosphoric acid, at least about 0.01 mg/l of isoproterenol, at least about 0.1 mg/l of guanosine 3',5'-cyclic monophosphate, at least about $10^{-7}$ g/l of hydrocortisone, at least about $10^{-7}$ g/l of epidermal growth factor, at least about 0.01 mg/l of fibroblast growth factor, at least about 10 mg/l of insulin, at least about 1 mg/l of transferrin and a source of at least about 1 mg/l of selenium, at least part of said medium having been conditioned, prior to contact with said cells, with Spodoptera frugiperda cells.

2. A process according to claim 1 wherein said venom gland tissue is removed from a larva or pupa of P. triplarinus.

3. A process according to claim 1 wherein said protease comprises trypsin.

4. A process according to claim 3 wherein said removed venom gland tissue is subjected to said trypsin in a saline substantially free of calcium and magnesium.

5. A process according to claim 4 wherein said removed venom gland tissue is exposed to said trypsin in said saline solution for a period of at least about 12 hours at a temperature not in excess of about 10° C., a trypsin inhibitor is then added to inhibit said trypsin and said removed venom gland tissue is teased apart to dissociate the cells therein.

6. A process according to claim 1 wherein said carbohydrate comprises at least one of the sugars fructose, glucose and sucrose.

7. A process according to claim 1 wherein said amino acids comprise the levo isomers of alanine, arginine, asparagine, aspartic acid, glutamic acid, glutamine, glycine, histidine, isoleucine, leucine, lysine, methionine, phenylalanine, proline, serine, threonine, tryptophan, valine, tyrosine and cysteine.

8. A process according to claim 1 wherein said medium contains the ions $Na^+$, $K^+$, $Mg^{2+}$, $Cl^-$, $SO_4^{2-}$ and $PO_4^{3-}$.

9. A process according to claim 1 wherein said medium comprises at least one polycarboxylic acid selected from the group consisting of citric, alpha-ketoglutaric, fumaric, malic and succinic acids.

10. A process according to claim 1 wherein said medium comprises at least one of the vitamins thiamine, riboflavin, pantothenic acid, pyridoxine, p-aminobenzoic acid, folic acid, niacin, isoinositol and biotin.

11. A process according to claim 1 wherein said medium comprises choline.

12. A process according to claim 1 wherein said medium comprises at least one protein.

13. A process according to claim 12 wherein said protein comprises at least one of bovine plasma albumin, fetal bovine serum, the soluble fraction of autolyzed fresh yeast and lactalbumin hydrolysate.

14. A process according to claim 1 wherein said selenium is present as an alkali metal selenate.

15. A process according to claim 1 wherein said medium is buffered with N,N-bis[2-hydroxyethyl]-2-aminoethane sulfonic acid.

16. A process according to claim 15 wherein said N,N-bis[2-hydroxyethyl]-2-aminoethane sulfonic acid is present in said medium in a concentration of at least about 0.1M.

17. A process according to claim 1 wherein said medium comprises at least about 0.01 mg/l of pyridoxal.

18. A process according to claim 1 wherein said medium comprises at least about 1 gl/l of trehalose.

19. A process according to claim 1 wherein said medium comprises an antibacterial agent.

20. A process according to claim 1 wherein said medium has substantially the following composition:

|  | mg/l. |
|---|---|
| $Na^+$ | 436 |
| $K^+$ | 1192 |
| $Mg^{2+}$ | 270 |
| $Ca^{2+}$ | 300 |
| $SO_4^{2-}$ | 1067 |
| $PO_4^{3-}$ | 312 |
| Fructose | 1700 |
| Glucose | 4400 |
| Sucrose | 400 |
| L-alanine | 145 |
| L-arginine | 133 |
| L-asparagine (as monohydrate) | 380 |

-continued

| | mg/l. |
|---|---|
| L-aspartic acid | 320 |
| L-glutamic acid | 929 |
| L-glutamine | 1620 |
| L-glycine | 872 |
| L-histidine | 371 |
| L-isoleucine | 191 |
| L-leucine | 197 |
| L-lysine (as hydrochloride) | 1638 |
| L-methionine | 74 |
| L-phenylalanine | 120 |
| L-proline | 350 |
| L-serine | 136 |
| L-threonine | 613 |
| L-tryptophan | 100 |
| L-valine | 475 |
| L-tyrosine | 30 |
| L-cystine | 80 |
| Citric acid | 500 |
| Alpha-ketoglutaric acid | 450 |
| Fumaric acid | 550 |
| Malic acid | 670 |
| Succinic acid | 660 |
| Thiamine (as hydrochloride) | 0.02 |
| Riboflavin | 0.02 |
| Pantothenic acid (as Ca salt) | 0.02 |
| Pyridoxine (as hydrochloride) | 0.02 |
| p-Aminobenzoic acid | 0.02 |
| Folic acid | 0.02 |
| Niacin | 0.02 |
| Isoinositol | 0.02 |
| Biotin | 0.01 |
| Choline chloride | 20 |
| BES | 17000 |
| Bovine plasma albumin | 10 |
| Fetal bovine serum | 50 ml |
| TC yeastolate | 3000 |
| Lactalbumin hydrolysate | 3000 |
| Epidermal growth factor | 0.0018 |
| Insulin | 105 |
| Transferrin | 5 |
| Selenium | 5 |
| Trehalose | 2000 |
| Fibroblast growth factor | 0.025 |
| Hydrocortisone | 0.0002 |
| Guanosine 3',5'-cyclic monophosphate | 0.35 |
| Garamycin | 50 |
| Adenosine 3',5-cyclic monophosphoric acid | 8780 |
| Isoproterenol | 0.0125 |
| Pyridoxal | 0.02. |

21. A cell culture comprising a plurality of cells from the venom gland of *Pseudomyrmex triplarinus* in contact with a cell culture medium substantially isotonic with said cells, said medium having a pH of about 7 and comprising at least about 5 g/l of carbohydrate, at least about 4 g/l of aminoacids, at least about 4 g/l of adenosine 3',5'-cyclic monophosphoric acid, at least about 0.01 mg/l of isoproterenol, at least about 0.1 mg/l of guanosine 3',5'-cyclic monophosphate, at least about $10^{-7}$ g/l of hydrocortisone, at least about $10^{-7}$ g/l of epidermal growth factor, at least about 0.01 mg/l of fibroblast growth factor, at least about 10 mg/l of insulin, at least about 1 mg/l of transferrin and a source of at least about 1 mg/l of selenium, at least part of said medium having been conditioned, prior to contact with said cells, with *Spodoptera frugiperda* cells.

22. A cell culture according to claim 21 wherein said culture medium is buffered with N,N-bis[2-hydroxyethyl]-2-aminoethane sulfonic acid.

23. A cell culture according to claim 21 wherein said medium has substantially the following composition:

| | mg/l. |
|---|---|
| Na$^+$ | 436 |
| K$^+$ | 1192 |
| Mg$^{2+}$ | 270 |
| Ca$^{2+}$ | 300 |
| SO$_4^{2-}$ | 1067 |
| PO$_4^{3-}$ | 312 |
| Fructose | 1700 |
| Glucose | 4400 |
| Sucrose | 400 |
| L-alanine | 145 |
| L-arginine | 133 |
| L-asparagine (as monohydrate) | 380 |
| L-aspartic acid | 320 |
| L-glutamic acid | 929 |
| L-glutamine | 1620 |
| L-glycine | 872 |
| L-histidine | 371 |
| L-isoleucine | 191 |
| L-leucine | 197 |
| L-lysine (as hydrochloride) | 1638 |
| L-methionine | 74 |
| L-phenylalanine | 120 |
| L-proline | 350 |
| L-serine | 136 |
| L-threonine | 613 |
| L-tryptophan | 100 |
| L-valine | 475 |
| L-tyrosine | 30 |
| L-cystine | 80 |
| Citric acid | 500 |
| Alpha-ketoglutaric acid | 450 |
| Fumaric acid | 550 |
| Malic acid | 670 |
| Succinic acid | 660 |
| Thiamine (as hydrochloride) | 0.02 |
| Riboflavin | 0.02 |
| Pantothenic acid (as Ca salt) | 0.02 |
| Pyridoxine (as hydrochloride) | 0.02 |
| p-Aminobenzoic acid | 0.02 |
| Folic acid | 0.02 |
| Niacin | 0.02 |
| Isoinositol | 0.02 |
| Biotin | 0.01 |
| Choline chloride | 20 |
| BES | 17000 |
| Bovine plasma albumin | 10 |
| Fetal bovine serum | 50 ml |
| TC yeastolate | 3000 |
| Lactalbumin hydrolysate | 3000 |
| Epidermal growth factor | 0.0018 |
| Insulin | 105 |
| Transferrin | 5 |
| Selenium | 5 |
| Trehalose | 2000 |
| Fibroblast growth factor | 0.025 |
| Hydrocortisone | 0.0002 |
| Guanosine 3',5'-cyclic monophosphate | 0.35 |
| Garamycin | 50 |
| Adenosine 3',5-cyclic monophosphoric acid | 8780 |
| Isoproterenol | 0.0125 |
| Pyridoxal | 0.02. |

24. A cell culture medium having an osmotic pressure of substantially 500 milliosmols, said medium having a pH of about 7 and comprising at least about 5 g/l of carbohydrate, at least about 4 g/l of aminoacids, at least about 4 g/l of adenosine 3',5'-cyclic monophosphoric acid, at least about 0.01 mg/l of isoproterenol, at least about 0.1 mg/l of guanosine 3',5'-cyclic monophosphate, at least about $10^{-7}$ g/l of hydrocortisone, at least about $10^{-7}$ g/l of epidermal growth factor, at least about 0.01 mg/l of fibroblast growth factor, at least about 10 mg/l of insulin, at least about 1 mg/l of transferrin and a source of at least about 1 mg/l of assimilable selenium.

25. A cell culture medium according to claim 24 wherein said carbohydrate comprises at least one of the sugars fructose, glucose and sucrose.

26. A cell culture medium according to claim 24 wherein the aminoacids comprise the levo isomers of alanine, arginine, asparagine, aspartic acid, glutamic acid, glutamine, glycine, histidine, isoleucine, leucine, lysine, methionine, phenylalanine, proline, serine, threonine, tryptophan, valine, tyrosine and cysteine.

27. A cell culture medium according to claim 24 containing the ions $Na^+$, $K^+$, $Mg^{2+}$, $Ca^{2+}$, $Cl^-$, $SO_4^{2-}$ and $PO_4^{3-}$.

28. A cell culture medium according to claim 24 further comprising at least one polycarboxylic acid selected from the group consisting of citric, alpha-ketoglutaric, fumaric, malic and succinic acids.

29. A cell culture medium according to claim 24 further comprising at least one of the vitamins thiamine, riboflavin, pantothenic acid, pyridoxine, p-aminobenzoic acid, folic acid, niacin, isoinositol and biotin.

30. A cell culture medium according to claim 24 further comprising choline.

31. A cell culture medium according to claim 24 further comprising at least one protein.

32. A cell culture medium according to claim 26 wherein said protein comprises at least one of bovine plasma albumin, fetal bovine serum, the soluble fraction of autolyzed fresh yeast and lactalbumin hydrolysate.

33. A cell culture medium according to claim 24 wherein said selenium is present as an alkali metal selenate.

34. A cell culture medium according to claim 29 buffered with N,N-bis[2-hydroxyethyl]-2-aminoethane sulfonic acid.

35. A cell medium according to claim 34 wherein said N,N-bis[2-hydroxyethyl]-2-aminoethane sulfonic acid is present in a concentration of at least about 0.1M.

36. A cell culture medium according to claim 24 further comprising at least about 0.01 mg/l of pyridoxal.

37. A cell culture medium according to claim 24 further comprising at least about 1 g/l of trehalose.

38. A cell culture medium according to claim 24 further comprising an antibacterial agent.

39. A cell culture medium according to claim 24 which has been conditioned with *Spodoptera frugiperda* cells.

* * * * *